(12) United States Patent
Rafiee et al.

(10) Patent No.: US 11,134,934 B2
(45) Date of Patent: Oct. 5, 2021

(54) DEVICES AND METHODS FOR CLOSING OPENINGS IN TISSUE STRUCTURES

(71) Applicant: Transmural Systems LLC, Andover, MA (US)

(72) Inventors: Nasser Rafiee, Andover, MA (US); Stuart MacDonald, Andover, MA (US); Ozgur Kocaturk, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 0 days.

(21) Appl. No.: 16/995,330

(22) Filed: Aug. 17, 2020

(65) Prior Publication Data

US 2020/0383668 A1 Dec. 10, 2020

Related U.S. Application Data

(63) Continuation-in-part of application No. PCT/US2019/050694, filed on Sep. 11, 2019.
(Continued)

(51) Int. Cl.
*A61B 17/00* (2006.01)
*A61F 2/24* (2006.01)

(52) U.S. Cl.
CPC .... *A61B 17/0057* (2013.01); *A61B 17/00234* (2013.01); *A61F 2/2427* (2013.01);
(Continued)

(58) Field of Classification Search
CPC .......... A61B 17/0057; A61B 17/12122; A61B 17/12172; A61B 17/12031; A61B 17/12136; A61B 17/12022; A61B 2017/00243; A61B 2017/00575; A61B 2017/00592; A61B 2017/1205;
(Continued)

(56) References Cited

U.S. PATENT DOCUMENTS 6,152,144 A    11/2000 Lesh et al.
6,689,150 B1    2/2004 Van Tassel
(Continued)

FOREIGN PATENT DOCUMENTS

EP    2626011 A2    8/2013
RU    128101 U1    5/2013
WO    20200056058 A1    3/2020

OTHER PUBLICATIONS

International Search Report dated Dec. 18, 2019 in International Application No. PCT/US2019/50694.

*Primary Examiner* — Mohamed G Gabr
(74) *Attorney, Agent, or Firm* — Winthrop & Weinstine, P.A.; Brian R. Pollack, Esq.

(57) ABSTRACT

In accordance with the disclosure, devices are provided for closing an opening in tissue. The devices include a proximal portion configured and arranged to occlude the tissue opening, and a distal anchor portion configured and arranged to anchor the device in the tissue opening. If desired, the distal anchor portion can be moved proximally or distally with respect to the proximal portion during implantation. The proximal portion can be configured and arranged to fit into a left atrial appendage of a patient, and further wherein the distal anchor portion is configured and arranged to extend into the left atrial appendage.

16 Claims, 13 Drawing Sheets

Related U.S. Application Data

(60) Provisional application No. 62/730,688, filed on Sep. 13, 2018.

(52) U.S. Cl.
CPC .. *A61F 2/2466* (2013.01); *A61B 2017/00243* (2013.01); *A61B 2017/00623* (2013.01); *A61B 2017/00632* (2013.01)

(58) Field of Classification Search
CPC . A61B 2017/00606; A61B 2017/00615; A61F 2/2418; A61F 2/2436; A61F 2/2457; A61F 2/2409; A61F 2/2454; A61F 2/01; A61F 2/2451; A61F 2/2466; A61F 2/88; A61F 2/90; A61F 2/966; A61F 2220/0008; A61F 2250/0003; A61F 2250/006; A61F 2230/0006; A61F 2230/0045; A61F 2230/0069; A61F 2230/0071; A61F 2230/0076; A61F 2230/008; A61F 2230/0091

See application file for complete search history.

(56) References Cited

U.S. PATENT DOCUMENTS

| | | | |
|---|---|---|---|
| 7,303,526 B2 | 12/2007 | Sharkey et al. | |
| 7,597,704 B2 | 10/2009 | Frazier et al. | |
| 10,045,765 B2 | 8/2018 | Rafiee et al. | |
| 10,143,478 B2 | 12/2018 | Forbes | |
| 10,321,998 B2 | 6/2019 | Rafiee et al. | |
| 10,398,551 B2 | 9/2019 | Rafiee et al. | |
| 10,433,962 B2 | 10/2019 | Rafiee et al. | |
| 10,449,046 B2 | 10/2019 | Rafiee et al. | |
| 2004/0034366 A1 | 2/2004 | Van Der Burg et al. | |
| 2006/0212047 A1 | 9/2006 | Abbott et al. | |
| 2006/0247672 A1 | 11/2006 | Vidlund et al. | |
| 2008/0015635 A1 | 1/2008 | Olsen et al. | |
| 2010/0211046 A1 | 8/2010 | Adams | |
| 2011/0082495 A1* | 4/2011 | Ruiz | A61B 17/0057 606/213 |
| 2011/0178539 A1 | 7/2011 | Homes, Jr. et al. | |
| 2012/0065667 A1 | 3/2012 | Javois et al. | |
| 2013/0172978 A1* | 7/2013 | Vidlund | A61F 2/2439 623/1.12 |
| 2013/0317541 A1 | 11/2013 | Singhal et al. | |
| 2014/0277074 A1 | 9/2014 | Kaplan et al. | |
| 2015/0223934 A1* | 8/2015 | Vidlund | A61F 2/2412 623/2.11 |
| 2015/0250590 A1* | 9/2015 | Gries | A61B 17/0401 623/2.11 |
| 2017/0014113 A1* | 1/2017 | Ma | A61B 17/12122 |
| 2017/0035433 A1* | 2/2017 | Forbes | A61B 17/12031 |
| 2018/0008248 A1* | 1/2018 | Rafiee | A61B 17/0057 |

* cited by examiner

DEVICES AND METHODS FOR CLOSING OPENINGS IN TISSUE STRUCTURES

CROSS-REFERENCE TO RELATED APPLICATIONS

This patent application claims the benefit of priority to International Patent Application No. PCT/US2019/050694, filed Sep. 11, 2019, which in turn claims the benefit of priority to U.S. Provisional Patent Application No. 62/730,688, filed Sep. 13, 2018. Each of the foregoing patent applications is hereby incorporated by reference herein in its entirety for all purposes whatsoever.

FIELD

This application relates to endovascular occlusion devices for use in closing openings in tissue structures, such as left atrial appendages.

BACKGROUND

Atrial fibrillation, which is an irregular and rapid heartbeat can lead to blood clot formation in the Left Atrial Appendage (LAA). Clots that form and escape from the LAA may circulate to other organs, block blood flow, and cause stroke. The present disclosure is directed to improved techniques and systems that can be used to address deficiencies in the art.

SUMMARY

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

Some devices presently exist for closing off the left atrial appendage, such as the Watchman™ device sold by Boston Scientific Corporation, illustrated in FIGS. 1A-1B. Such devices act to isolate the LAA from atrium cavity, with the goal of preventing clots from escaping from the LAA. Conventional devices typically include a single piece, pre-shaped and covered with a fabric or mesh that can be deployed into the orifice of LAA through a delivery catheter.

However, Applicant has come to appreciate that the devices known in the art can be difficult to align and secure. Applicant has also come to appreciate that the shape of the LAA can vary from patient to patient. However, devices, such as the Watchman™ device are specifically configured for circular orifices, and may not fit properly in the LAA, depending on the patient. Applicant has come to appreciate that it would be advantageous for such a device to be configured and arranged to self-align with the LAA. Applicant has also come to appreciate that such devices would also benefit significantly from having structural features to provide enhanced securement, as this may help to cause proper orientation and prevent alignment problems during placement, as well as to help to prevent device migration and device dislodgement.

Disclosed herein, in some implementations, are left atrial appendage closure devices and related systems and methods.

In accordance with the disclosure, devices are provided for closing an opening in tissue. The devices include a proximal portion configured and arranged to occlude the tissue opening, and a distal anchor portion configured and arranged to anchor the device in the tissue opening.

If desired, the distal anchor portion can be moved proximally or distally with respect to the proximal portion during implantation. The proximal portion can be configured and arranged to fit into a left atrial appendage of a patient, and further wherein the distal anchor portion is configured and arranged to extend into the left atrial appendage. The distal anchor portion can be configured and arranged to anchor itself against or into a wall defined by a left atrial appendage. The distal anchor portion can be configured and arranged to pierce through a wall of a left atrial appendage and anchor itself against epicardial tissue of the heart. If desired, the distal anchor portion can be discrete from the proximal portion.

In various implementations, the proximal portion can include an expandable framework covered by a layer of occlusive material. The proximal portion can be formed from a self-expanding mesh body formed from overlapping filaments. The distal anchor portion can be formed from an expandable braided disc. The mesh body and braided disc can be longitudinally displaceable with respect to one another. The mesh body and braided disc can be connected by an elastic member configured to pull the mesh body and braided disc toward each other. The proximal portion can include a structural framework formed from a plurality of pre-shaped individual wires. The pre-shaped individual wires can be coupled to each other by a banding material. The pre-shaped individual wires can be coupled to a membrane material that at least partially defines the proximal portion of the device. The pre-shaped individual wires can be configured and arranged to move with respect to each other and be separated and spaced from each other. In some implementations, the proximal portion can include a structural framework formed from a laser cut shape memory material. If desired, proximal portion is formed at least in part from shape memory material. Moreover, the proximal portion can be covered at least in part by a fabric, polymeric or tissue layer. In various embodiments, the proximal portion can be coaxial with and surrounds the distal anchoring portion.

In further implementations, the proximal portion and distal anchoring portion can be adjustably connected by a hollow suture material. A lock can be provided that is secured to the hollow suture material to secure the relative position of the proximal portion and the distal anchoring portion. Tension is preferably maintained in the suture to hold the proximal portion in place. A delivery catheter can be provided including these components coupled thereto, wherein the delivery catheter includes a push rod or tube slidably disposed inside of the suture material, the push rod or tube can be configured to push the distal anchoring member through to the epicardium outside of the LAA.

In some implementations, the system can include two coaxial and independently deployable implant structures. A proximal structure can be provided with an outer layer that covers a structural frame portion made, for example, from shape memory material. This aspect can be similar in some aspects to the Watchman™ device, in that the proximal portion is generally configured into the opening of the LAA. The system also includes an inner, and in some implementations, distal, structure that includes at least one distal anchor that can be deployed after the distal structure reaches the surface of the epicardium beyond the LAA.

Alternatively, an anchor can be provided that anchors into the tissue of the LAA, such as the tissue that surrounds and defines the LAA. In some implementations, the anchor can be configured as a spiral, flat-strip or wing configuration that can be prepared using shape memory metal alloys. The inner or distal portion can be connected to a hollow suture that has one or more pre-shaped ties, and/or a discrete locking device that is configured and arranged to secure the proximal end of the system to the inner/distal portion of the system. For example, this can be done after applying a desired amount of tension to compress the proximal portion of the device into a neck region of the LAA.

The proximal portion of the device can have a frame formed, for example, using pre-shaped individual nitinol wires, nitinol braiding or having a stent-like geometry including strut rings, and the like, formed by way of laser cutting systems. The outer layer of the proximal portion of the system can be formed by one or more of elastic silicone, epoxy, polyurethane coating or medical fabric mesh such as polyester fabric, and the like.

The disclosure further provides a system including a delivery catheter having a proximal end and a distal end. The distal end of the delivery catheter can be coupled to a prosthesis device and anchor as described herein, wherein the distal anchoring portion of the device can be pulled with respect to the proximal portion by the delivery system to create tension between the proximal portion of the device and the distal anchoring portion of the device in order to help seat the device in the LAA or other tissue orifice.

If desired, the system can further include a lock for locking the distal anchoring portion to the proximal portion to maintain the relative position of the distal anchoring portion to the proximal portion. The proximal portion and the distal anchoring portion can be connected to the proximal portion by way of a hollow tether. The proximal portion of the device can define a central lumen therethrough for permitting passage of the distal anchoring portion. If desired, the proximal portion can define a recess therein for receiving the lock when the lock is affixed to the distal anchoring portion. The delivery catheter can include an inner portion that is configured to be advanced distally through the proximal portion of the device until the inner portion of the delivery system contacts an inner wall of the left atrial appendage. In various embodiments, the inner portion of the delivery catheter includes a hollow passage for advancing the distal anchoring portion of the device therethrough.

The disclosure further provides methods of closing an opening in tissue, such as closing a left atrial appendage. The method includes providing a system as described herein, disposing the distal end of the delivery catheter proximate a left atrial appendage (LAA) of a patient, deploying the proximal portion of the prosthesis in an opening of the LAA to isolate an interior volume of the LAA from the left atrium, anchoring the distal anchoring portion of the device with respect to the LAA, and applying tension between the proximal portion and distal anchoring portion to hold the proximal portion in place in the opening of the LAA.

In some implementations, the method can further include pulling a portion of the LAA against the proximal portion of the device. The method can still further include locking the relative position of the proximal portion and distal anchoring portion by applying a lock that locks the proximal portion to the distal anchoring portion. If desired, the method can further include releasing the lock and the tension, and adjusting the position of the proximal portion of the device, and reapplying a desired amount of tension, and reapplying the lock. Anchoring the distal anchoring portion of the device can include directing a distal end of the distal anchoring portion through to the epicardium, deploying an anchor radially outwardly, and pulling the anchor against the epicardium while pulling the proximal portion of the device toward the anchor. The method can further include confirming positioning of the proximal portion in the LAA under direct utilization, and locking the distal anchoring portion to the proximal portion. The method can still further include directing a cutting catheter to the proximal portion of the device, and severing a tether connecting the device to the delivery catheter. The cutting catheter can include a sleeve that is configured to slide along the tether.

The disclosure further provides implementations of an implant to occlude a left atrial appendage (LAA) in the heart that includes a distal anchor having a first expanded portion situated in the pericardial cavity and a second expanded portion situated inside the LAA, wherein a neck portion of the distal anchor traverses an opening formed in the wall of the LAA from inside the heart into the pericardial cavity, and a LAA occluder expanded into the LAA to occlude a substantial volume of the LAA, the LAA occluder being removably coupled to the distal anchor.

In some implementations, the LAA occluder is removably coupled to the distal anchor by a threaded connection, a keyed connection, a lock that can be engaged or disengaged, or another type of connection. If desired, a main body portion of the LAA occluder can be coupled to at least one length limiting tether that connects to a first coupling, wherein the first coupling of the LAA occluder is configured to couple to the distal anchor.

If desired, the distal anchor can be displaceable proximally or distally with respect to the proximal portion during implantation. The LAA occluder can include an expandable framework covered by a layer of occlusive material. The LAA occluder can be formed from a self-expanding mesh body formed from overlapping filaments. The distal anchor can be formed from a plurality of expandable braided discs. The distal anchor and LAA occluder can be connected at least in part by an elastic member that pulls the distal anchor toward the LAA occluder. The distal anchor and LAA occluder can be connected at least in part by a tension spring that pulls the distal anchor toward the LAA occluder. The distal anchor and LAA occluder can be connected at least in part by at least one length limiting tether.

In accordance with further implementations, the implant can further include at least one tether directed through the LAA occluder coupled to the distal anchor, wherein applying tension to the at least one tether draws the mesh body and braided disc closer together. The LAA occluder can include a structural framework formed from a laser cut shape memory material. The LAA occluder can be formed at least in part from shape memory material. The LAA occluder can be covered at least in part by a fabric, polymeric or tissue layer.

The disclosure further provides a system including a delivery catheter having a proximal end and a distal end, the distal end of the delivery catheter being coupled to an LAA occluder as described above, wherein the distal anchor can be pulled with respect to the LAA occluder by the delivery system to create tension between the LAA occluder and the distal anchor. The system can further include a lock to lock the distal anchor to the LAA occluder to maintain the relative position of the distal anchor to the LAA occluder. If desired, the LAA occluder and the distal anchor can be connected by way of a hollow tether.

The disclosure further provides a method of treating a left atrial appendage that includes anchoring a distal anchor of a system as described above across the wall of the left atrial appendage of a patient, disposing the distal end of the delivery catheter proximate a left atrial appendage (LAA) of a patient, coupling the LAA occluder to the distal anchor, and deploying the LAA occluder isolate an interior volume of the LAA from the left atrium. If desired, the method can further include locking the relative position of the LAA occluder and the distal anchor. The method can still further include unlocking the LAA occluder from the distal anchor and adjusting the relative position of the LAA occluder to the distal anchor, as desired.

The disclosure further provides embodiments of a cardiac implant that includes a distal anchor having a first expanded portion situated in the pericardial cavity and a second expanded portion situated within the apex of a ventricle, wherein a neck portion of the distal anchor traverses an opening formed in the wall of the heart proximate the apex of the ventricle from inside the heart into the pericardial cavity, and an artificial valve coupled to the distal anchor by at least one tether, the artificial valve being configured to be received in an annulus of a cardiac valve. If desired, the ventricle can be the left ventricle and the cardiac valve can be the mitral valve. Alternatively the ventricle can be the right ventricle and the valve can be the tricuspid valve.

If desired, the artificial valve can be removably coupled to the distal anchor. For example, the artificial valve can be removably coupled to the distal anchor by a mechanical coupling that can be engaged and disengaged.

A method of implanting an artificial mitral valve, including anchoring a distal anchor as described herein across the wall of a heart proximate the apex of the left ventricle, including deploying a distal radially expandable portion of the distal anchor within a pericardial cavity, coupling an artificial valve to the distal anchor after the distal anchor has been deployed, and deploying the artificial valve within a native mitral annulus.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE FIGURES

The foregoing and other objects, aspects, features, and advantages of exemplary embodiments will become more apparent and may be better understood by referring to the following description taken in conjunction with the accompanying drawings, in which.

DETAILED DESCRIPTION

Reference will now be made in detail to the present preferred embodiments of the disclosure, examples of which are illustrated in the accompanying drawings. The methods and corresponding steps of the disclosed embodiments will be described in conjunction with the detailed description of the systems.

In accordance with the disclosure, devices are provided for closing an opening in tissue. The devices include a proximal portion configured and arranged to occlude the tissue opening, and a distal anchor portion configured and arranged to anchor the device in the tissue opening.

Figure 2:
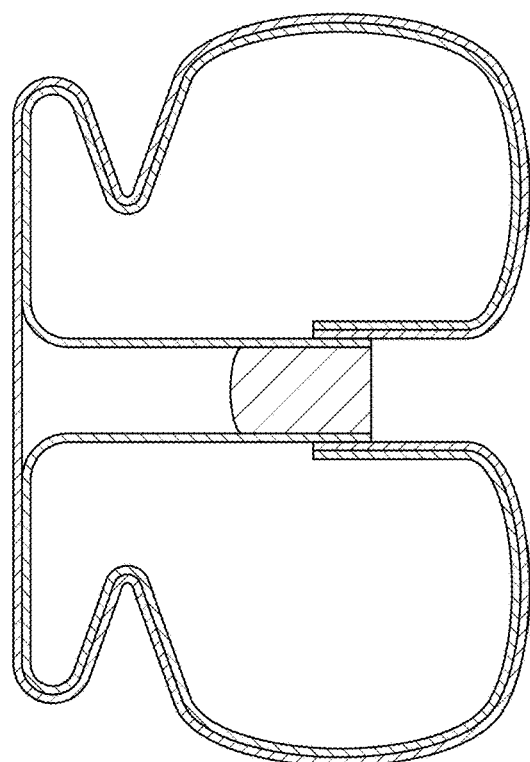
FIG. 2 is a cross-section of a proximal occluding portion of a first representative embodiment of a device in accordance with the present disclosure.
Figure 3:
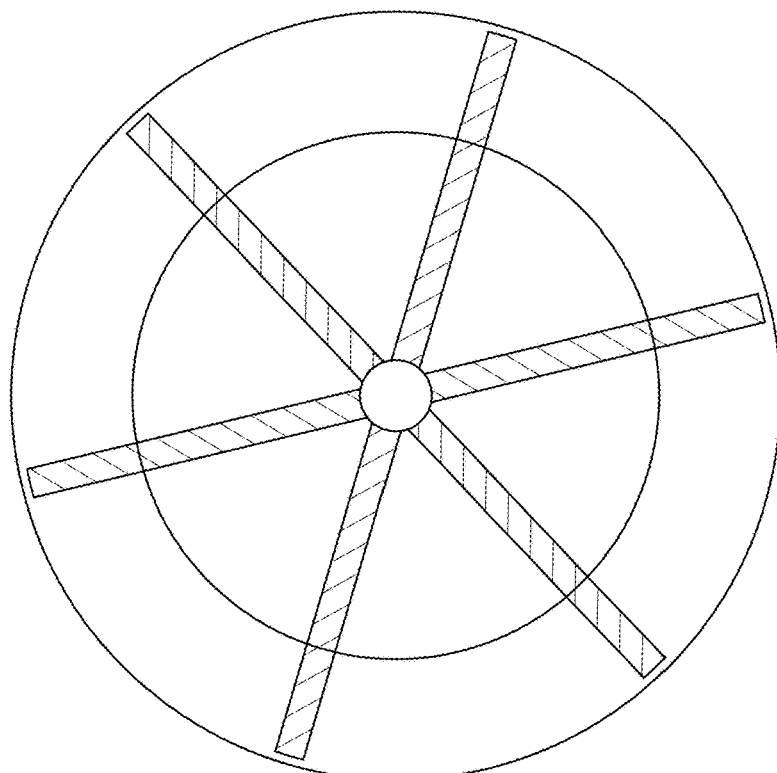
FIG. 3 is a top view of the proximal portion of a device illustrated in FIG. 2.
Figure 10:
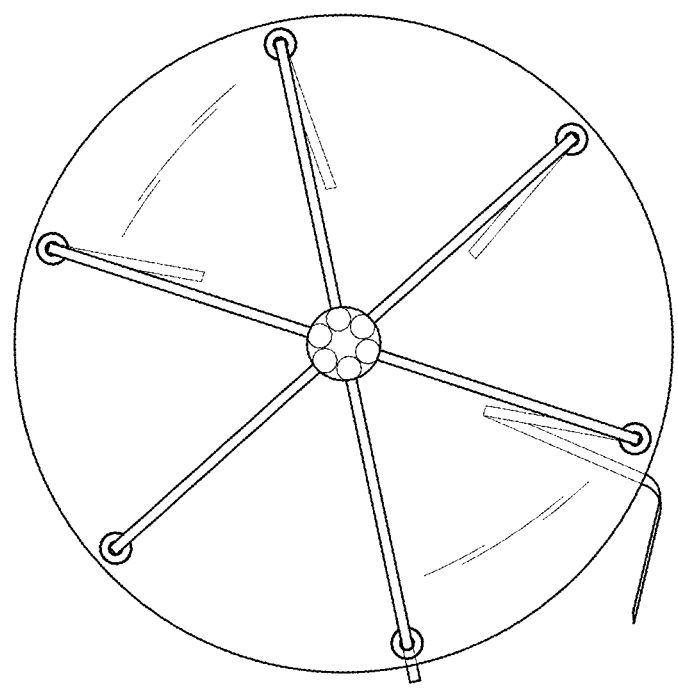
FIG. 10 is a top view of an occluder portion of a further device in accordance with the present disclosure.
Figure 11:
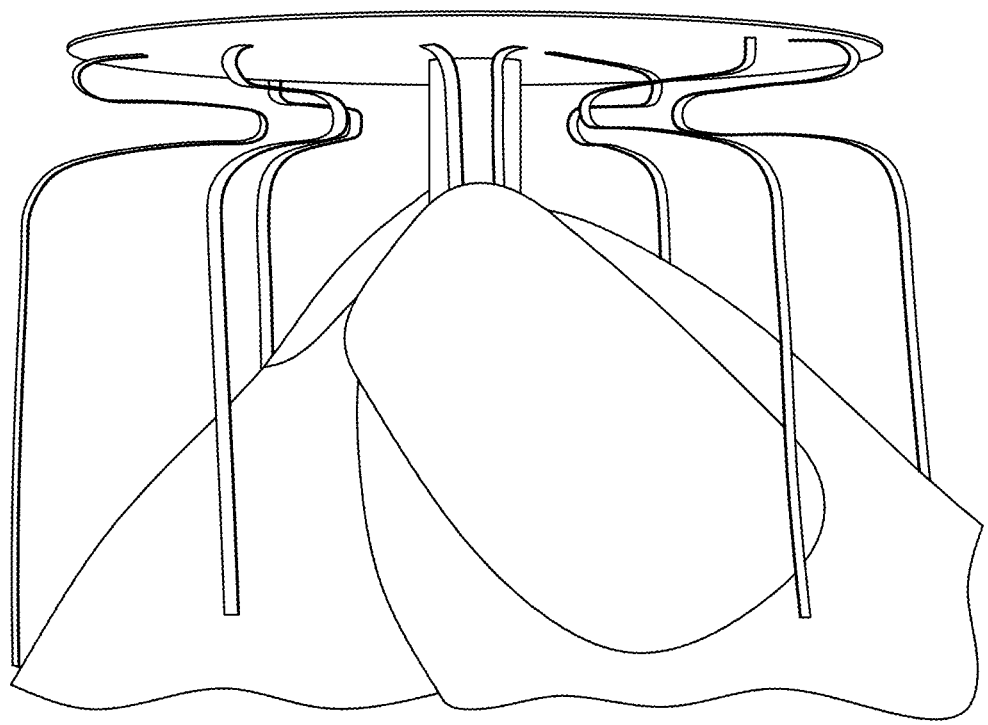
FIG. 11 is a side view of the embodiment of FIG. 10.

For purposes of illustration, and not limitation, FIG. 2 shows a cross sectional view of a proximal portion of a device in accordance with the disclosure. Specifically, FIG. 2 shows an occluder portion configured for attachment with a distal anchoring portion. The cross section in FIG. 2 shows the device in a proximal-distal orientation from left to right, and FIG. 3 shows a view of the proximal end of the device. As illustrated, the proximal end of the device includes a flange that necks down and then flares out to form a generally bell-shaped distal portion. Visible in FIG. 3 is a plurality, in this illustrate, six, structural bands that conform to the undulating surface of the embodiment. The bands can be formed from polymer or shape memory material, such as NiTi shape memory alloys, and be configured to expand to the illustrated shape when deployed. The shape memory bands can follow the surface of the embodiment as illustrated by the cross section of FIG. 2, wherein the bands start at the proximal end of the device, extend radially outwardly to the edge of the proximal flange, wrap around the edge of the flange and proceed radially inwardly, where they change direction at an inflection point and proceed radially outwardly, and then bend along a distal direction, and then bend radially inwardly at the distal end of the embodiment, and wrap around and proceed proximally to an attachment point, such as to an internally threaded sleeve, or nut. FIGS. 10-11 illustrate a further version of this embodiment, wherein a proximal disc is connected to a distal frame work formed from ribbons of shape memory NiTi material wherein the framework extends distally and does not wrap around proximally.

Figure 4:
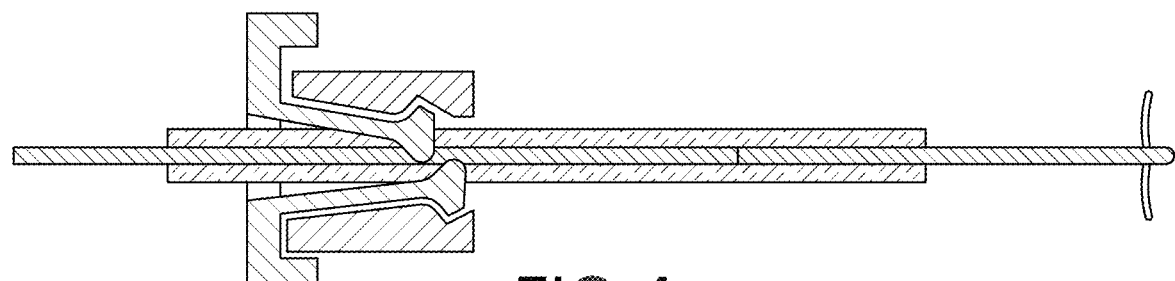
FIG. 4 is a view of a distal anchoring portion of a device in accordance with the present disclosure including a displaceable lock mounted thereon.
Figure 5:
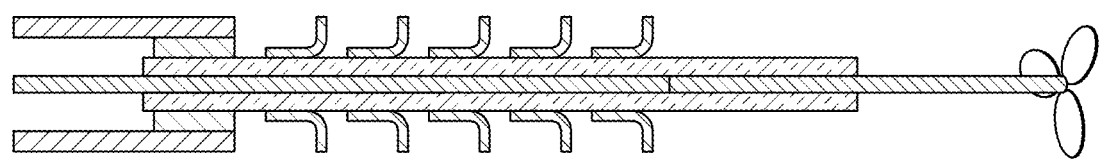
FIG. 5 is a view of a distal end portion of the embodiment illustrated in FIG. 4.

FIGS. 4 and 5 illustrate aspects of a distal anchoring portion and lock configured to mate with the proximal occluder portion illustrated in FIGS. 2 and 3. As illustrated, a distal anchor portion is provided that is configured to change in shape from a straight wire to a wire having one or more transverse loops at the distal end. After the proximal portion of the device of FIGS. 2-3 is implanted in the opening of the LAA while being removably attached to the distal end of a main shaft of a delivery tube portion of a delivery catheter, an inner tubular shaft that is slidably disposed within the main shaft of the delivery catheter (not shown) is advanced distally into the LAA to advance the combined structure of an elongate hollow suture attached to the distal metallic anchor wire to the wall of the LAA. The distal metallic wire is preferably fitted with a removable push rod or push tube at its proximal end that extends proximally out of the LAA and the patient along with the elongate suture. Once the distal end of the inner tubular shaft is at the wall of the LAA, the push tube or rod is then advanced distally with respect to the inner tubular shaft. The push tube or rod, which is constrained within and adjacent to the proximal end of the distal anchor wire, then pushes the distal anchor wire, and suture attached thereto, the distal anchor wire being straight while constrained inside of the distal end of the inner tubular shaft. The anchor wire, due to being attached to the distal region of the hollow suture, therefore pulls on the hollow suture when it is pushed distally by the push tube/rod. The anchor wire is then pushed out of the end of the inner tubular shaft and through the wall of the heart to a location outside of the heart to the epicardium within the pericardial cavity, where it resumes its heat set shape, for example, of one, two, three or four looped petals, or other winding shape. The tether is then pulled proximally, which, by virtue of being attached to the distal anchor wire, pulls on the distal anchor wire, which then pulls on the epicardium.

The push wire or tube is then removed from the proximal end of the anchor by withdrawing it proximally out of the hollow suture. The suture is then pulled proximally with respect to the main delivery tube of the delivery catheter to cause the central collar/threaded sleeve of the proximal portion of the device (illustrated in FIGS. 2-3) to be pulled closer to the distal anchor that in turn pulls inwardly on the epicardium. A lock can be advanced along the tether and snapped or otherwise fastened in place within the central sleeve of the proximal portion to hold the suture fast an in place and under tension, holding the proximal portion of the device in place in the entrance of the LAA. Alternatively, the suture can be provided with a plurality of barbs that face distally on an inclined angle, as illustrated in FIG. 5 made for example, from NiTi alloy or a polymer. Thus, when the suture is pulled through the sleeve of the proximal portion, the barbs deflect and are pulled through the opening of the central sleeve of the proximal portion of the device and snap back outward after passing through the opening, thereby preventing the suture from moving along a distal direction through the proximal portion of the device, holding the entire assembly in place.

Figure 6:
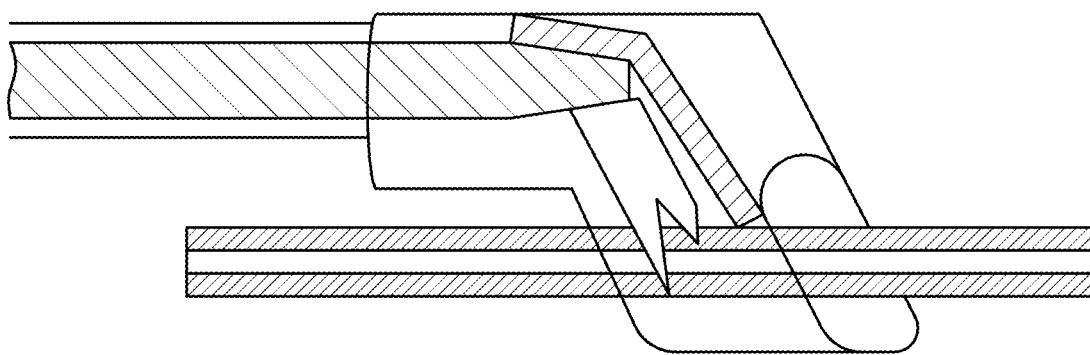
FIG. 6 is an illustration of an offset cutting catheter in accordance with the present disclosure.

Next, the main delivery tube can be decoupled from the fitting on the proximal portion of the device, and the main delivery tube, and inner tubular shaft, can be removed from the proximal portion of the device and withdrawn proximally over the tether, for example, through a guiding catheter that surrounds the main delivery tube, leaving the tether in place along the interior passage of the guiding catheter. Next, as illustrated in FIG. 6, a cutting catheter, such as an offset cutting catheter (or a cutting catheter similar to those described in U.S. patent application Ser. No. 15/796,344, which is incorporated by reference herein in its entirety), can be advanced along the hollow suture/tether to a location near the LAA. An offset angled "V"-shaped blade, as illustrated, can then be advanced transversely, or obliquely, across the tether, severing the tether. The tether and cutting catheter can be withdrawn and removed into the guiding catheter, and the guiding catheter can be removed from the patient. Any holes formed in tissue structures, such as the septum, to permit passage of the guiding catheter can be closed, for example, with a closure device, such as those described in U.S. patent application Ser. No. 15/664,642, which is incorporated by reference herein in its entirety.

FIG. 4 further illustrates features of a lock for locking the suture attached to the distal anchoring portion to the proximal portion to maintain the relative position of the distal anchoring portion to the proximal portion. The lock includes a proximal locking pin that includes a plurality of distal extensions that surround the wire. The extensions can be held in a distal housing wherein moving the housing and pin together can hold the lock in place fast against the suture. The lock can be discrete from the proximal portion of the implant, or be integrated with the proximal portion of the implant. By way of further example, if desired, the lock can resemble those illustrated in U.S. patent application Ser. No. 15/664,642. If desired, the proximal portion can define a recess therein for receiving the lock when the lock is affixed to the distal anchoring portion.

Figure 1A:
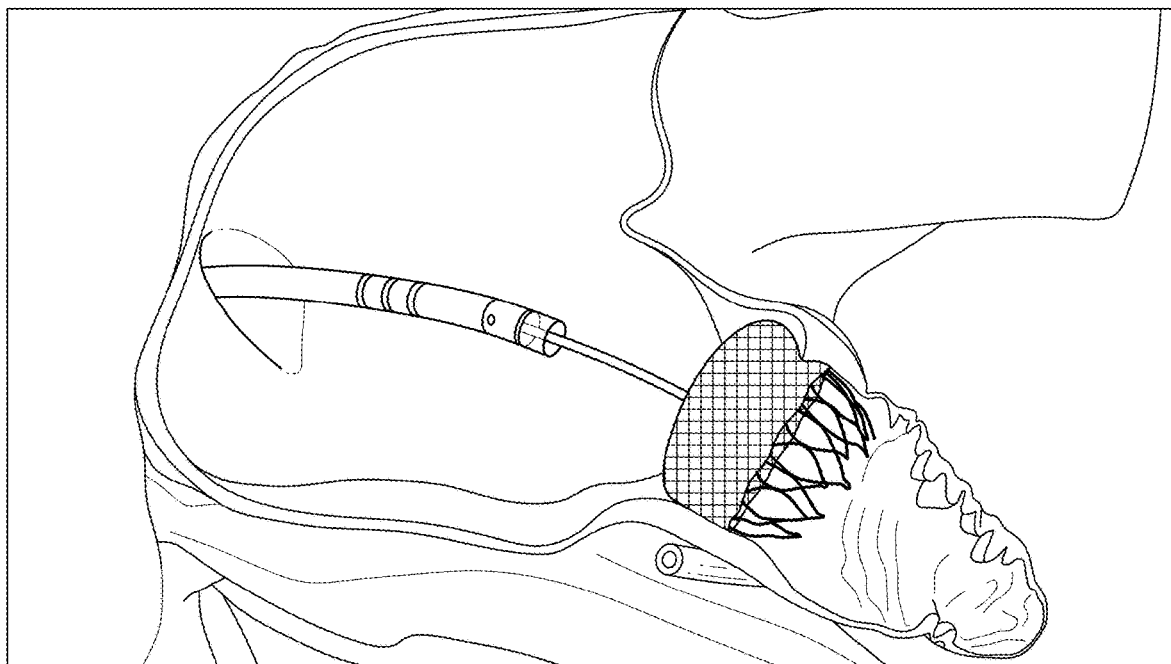
FIGS. 1A-1B are illustrations of a prior art device for isolating a left atrial appendage.
Figure 1B:
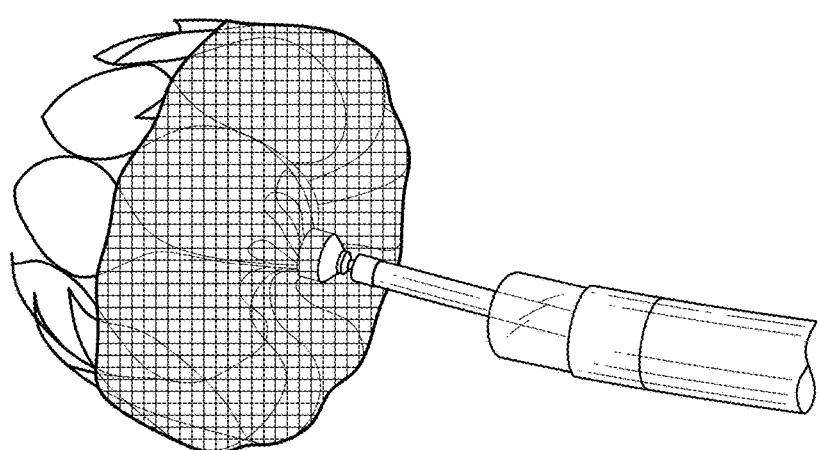
Figure 7:
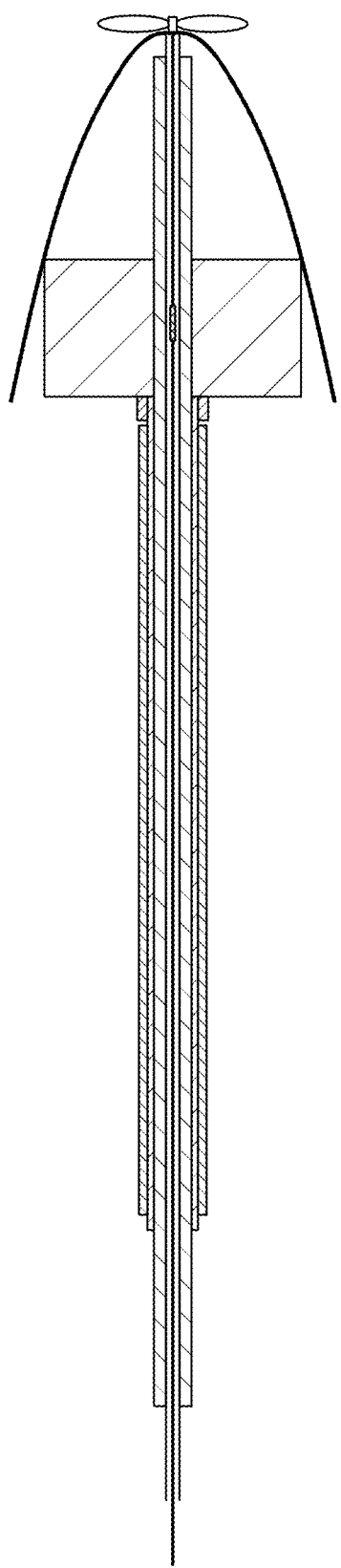
FIG. 7 is a schematic view of a device and associated delivery catheter in accordance with the present disclosure.

FIG. 7 presents a schematic view of an embodiment of a delivery system that can be used to perform the procedure described above, showing relative placement of the different components of the system, but not showing the guiding catheter, in which all components would be delivered. As can be seen with respect to the relative placement of components, the distal anchor portion can be moved proximally or distally with respect to the proximal isolation element portion of the device during implantation. The proximal portion/isolation element is configured and arranged to fit into a left atrial appendage of a patient, and may be umbrella or bell shaped as with the Watchman™ device illustrated above in FIGS. 1A-1B. As further illustrated in FIG. 7, the distal anchor portion is configured and arranged to extend into the left atrial appendage. While the distal anchor portion can be configured and arranged to anchor itself against or into a wall defined by a left atrial appendage, in FIG. 7 it is illustrated as piercing through an outer wall of a left atrial appendage and anchored against epicardial tissue of the heart within the pericardial cavity. As illustrated, the distal anchor portion can be discrete from the proximal portion. Alternatively, they can be attached, for example as discussed further below with respect to the embodiments of FIGS. 8 and 9.

The proximal portion of the device can be formed in a variety of manners. For example, the proximal portion of the device can include an expandable framework covered by a layer of occlusive material, as with the Watchman™ device. Alternatively, the proximal portion can be formed as a plug of material that expands into the LAA space.

Figure 8A:
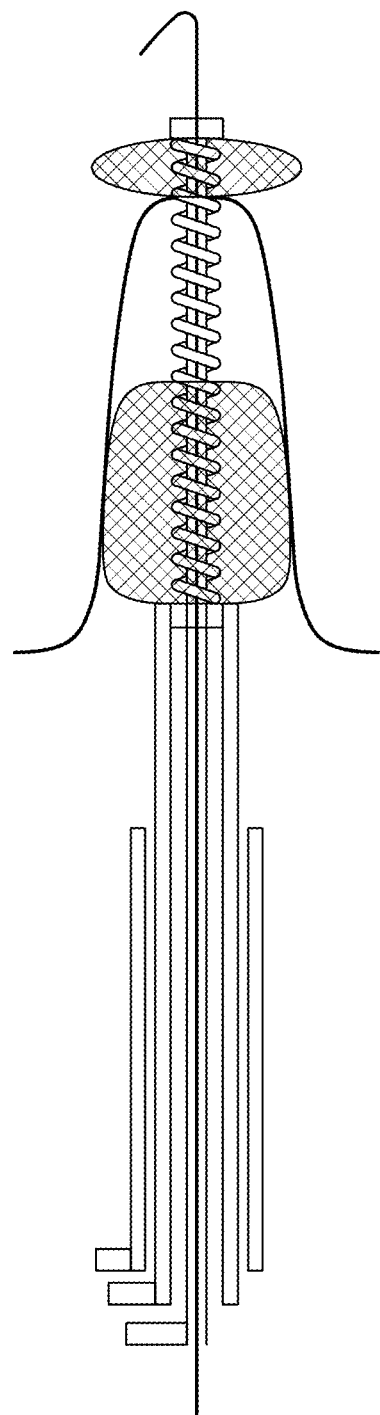
FIG. 8A is a schematic view of a further device and associated delivery catheter in accordance with the present disclosure.
Figure 8B:
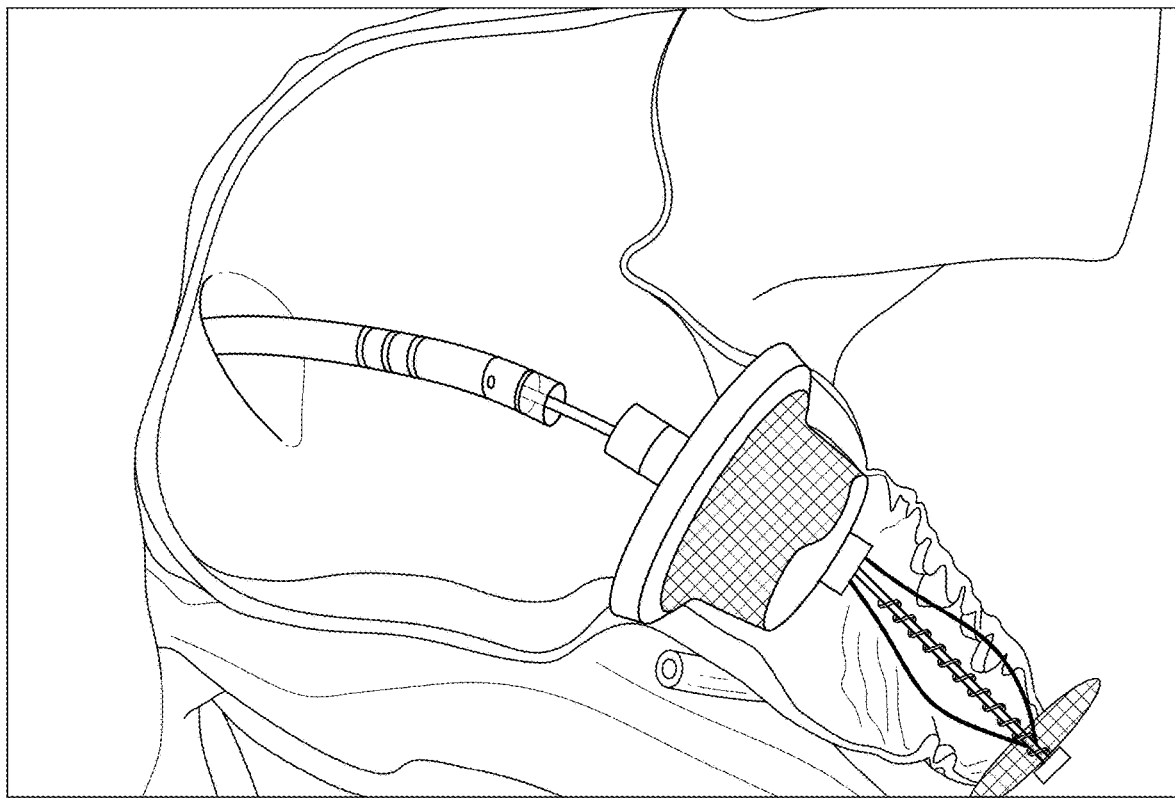
FIG. 8B is a schematic view of yet a further device and associated delivery catheter in accordance with the present disclosure.
Figure 9:
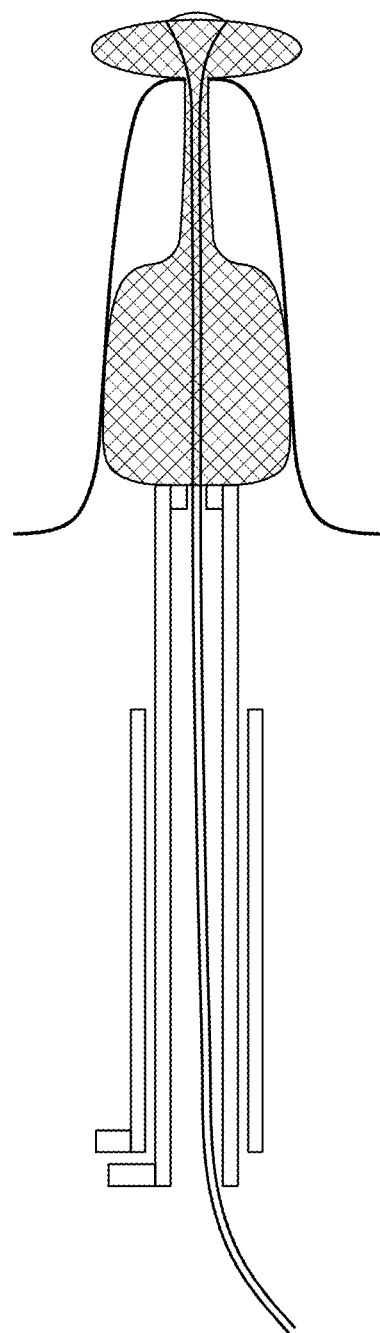
FIG. 9 is a schematic view of still a further device and associated delivery catheter in accordance with the present disclosure.

In a further embodiment, and as illustrated in FIGS. 8A and 9, the proximal portion of the device can be formed from a mesh body formed from overlapping filaments that can be self-expanding and formed from NiTi alloy or other materials. The distal anchor portion can be formed from an expandable braided disc. The mesh body and braided disc can be longitudinally displaceable with respect to one another. The mesh body and braided disc can be connected by an elastic member, as illustrated in FIG. 8A that is configured to pull the mesh body and braided disc toward each other, such as with embodiments illustrated in U.S. application Ser. No. 15/664,642. As illustrated in FIG. 8A, this prosthesis bears significant resemblance to those in U.S. Ser. No. 15/664,642, but wherein the proximal disc is configured to occupy a volume that is less disc-shaped and more plug-shaped, wherein the braided elements of the proximal disc or mesh conforms to the interior surface of the LAA, facilitating fit and anchoring, and reducing the chances of formation of emboli or clots. The interior of the mesh can be filled with fabric, graft or other material configured to facilitate sealing and isolation of the LAA from the volume of the adjacent atrium. FIG. 8B depicts a variation of the embodiment of FIG. 8A, wherein the LAA is coupled to the distal anchor by way of one or more length limiting tethers that can be configured to prevent the spring coupling the LAA to the anchor from being stretched beyond a desired magnitude.

Alternatively, the proximal portion of the device can alternatively include a structural framework formed from a plurality of pre-shaped individual wires. These pre-shaped individual wires can be coupled to each other by a banding material such as sutures, clips, sleeves, or radiopaque marker bands. The pre-shaped individual wires can additionally or alternatively be coupled to a membrane material that at least partially defines the proximal portion of the device. The pre-shaped individual wires can be configured and arranged to move with respect to each other and be separated and spaced from each other. In some implementations, the proximal portion can include a structural framework formed from a laser cut shape memory material. If desired, the proximal portion is formed at least in part from shape memory material. Moreover, the proximal portion can be covered at least in part by a fabric, polymeric or tissue layer. In various embodiments, the proximal portion can be coaxial with and surrounds the distal anchoring portion.

FIG. 9 illustrates an alternative embodiment of mesh body that deforms into a distal disc that rests outside the epicardium and a proximal disc, or volume, that rests in the LAA. The proximal and distal portions can be formed by the same mesh material, appropriately heat set into a desired shape that can then conform to the interior of the LAA. To shorten the length of the device and to hold it in place, a tether can be routed through the distal end of the implant at the epicardium, and routed through the implant and be externalized. A lock can then be slid along the tethers and tension can be imparted to the tethers, and the lock fixed in place at the proximal end of the implant. A cutting catheter as described herein or as described in U.S. Ser. No. 15/796,344 can then be slid down along the tethers to cut the tethers off near the proximal end of the implant.

As set forth above, the disclosure further provides methods of closing an opening in tissue, such as closing a left atrial appendage. It will be recognized that the disclosed techniques can be used to close other openings in tissues and organs. The methods typically include providing a system as described herein (e.g., FIGS. 2-9), disposing the distal end of a delivery catheter proximate a left atrial appendage (LAA) of a patient (e.g., FIGS. 7-9), deploying the proximal portion of the prosthesis in an opening of the LAA to isolate an interior volume of the LAA from the left atrium (e.g., FIG. 7), anchoring the distal anchoring portion of the device with respect to the LAA, and applying tension between the proximal portion and distal anchoring portion to hold the proximal portion in place in the opening of the LAA. Alternatively, the prosthesis can be provided in a single piece (e.g., FIGS. 8-9).

In some implementations, the method can further include pulling a portion of the LAA against the proximal portion of the device (e.g., FIG. 7). The method can still further include locking the relative position of the proximal portion and distal anchoring portion by applying a lock that locks the proximal portion to the distal anchoring portion (e.g., FIG. 4). If desired, the method can further include releasing the lock and the tension, and adjusting the position of the proximal portion of the device, and reapplying a desired amount of tension, and reapplying the lock. Anchoring the distal anchoring portion of the device can include directing a distal end of the distal anchoring portion through to the epicardium (e.g., FIG. 7), deploying an anchor radially outwardly, and pulling the anchor against the epicardium while pulling the proximal portion of the device toward the anchor. The method can further include confirming positioning of the proximal portion in the LAA under direct utilization, and locking the distal anchoring portion to the proximal portion. The method can still further include directing a cutting catheter to the proximal portion of the device (e.g., FIG. 6), and severing a tether connecting the device to the delivery catheter. The cutting catheter can include a sleeve that is configured to slide along the tether.

Figure 12:
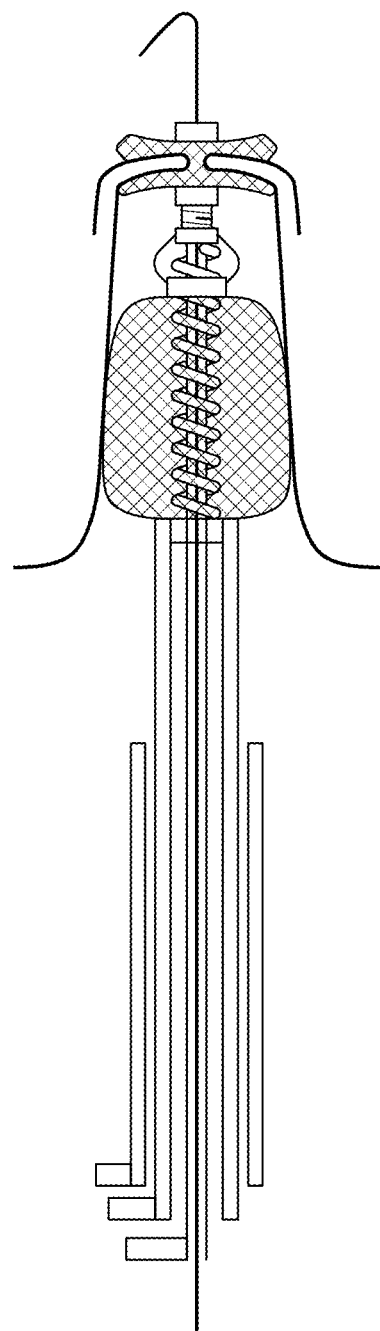
FIG. 12 is a schematic view of a further device and associated delivery catheter in accordance with the present disclosure to deliver a multiple piece implant to the LAA of a patient.

FIG. 12 is a schematic view of a further device and associated delivery catheter in accordance with the present disclosure to deliver a multiple piece implant to the LAA of a patient. As with the embodiments of FIGS. 8 and 9, the proximal portion of the device can be formed from a mesh body formed from overlapping filaments that can be self-expanding and formed from NiTi alloy or other materials as illustrated in U.S. application Ser. No. 15/664,642. As illustrated, the distal anchor portion can be formed from an implant formed from a pair of expandable braided discs as set forth, for example, in FIG. 1D of U.S. application Ser. No. 15/664,642. In the embodiment of FIG. 12, first, an anchor, such that in FIG. 1D of U.S. Ser. No. 15/664,642, is disposed in the outer wall of the LAA with the distal disc being located in the pericardial cavity, and the proximal disc being located inside the heart, wherein the two discs are pulled toward each other by a tension spring (not shown in FIG. 12). The proximal end of the implant includes a threaded male or female fastener that functions as a docking collar. Procedurally, the guidewire is first advanced through the wall of the heart into the pericardial cavity, and the implant is installed in the wall. Once it has been confirmed that the implant is firmly seated, it can serve as an anchor, and a docking station, to install the proximal portion of the overall implant to occlude the LAA. Specifically, the delivery catheter that delivers the anchor across the wall of the LAA can be unscrewed from the implant and withdrawn over the guidewire, and a second delivery catheter can be delivered over the guidewire with the proximal implant. The proximal implant can terminate in a complementary male or female threaded end that is then threadably received by the docking collar of the implant that has been installed. The retractable sheath of the delivery system, as depicted, can be withdrawn, and the proximal implant can be expanded to occupy the LAA cavity. The proximal implant is held firmly in place by way of its own expansion, and by the previously installed implant to which it is attached. Relative tension between the two implants can be established by a tension spring built into the proximal implant that tends to draw the implants together, with the net effect of wedging the proximal implant in place in the LAA. If desired, the LAA occluder can be provided with one or more length limiting tethers that connect the distal coupling of the LAA occluder with the proximal body of the LAA to prevent it from being overly stretched as illustrated in FIG. 12. Likewise, the LAA occluder can be provided with a collar at either end of the mesh body, and be connected to the distal coupling with a tension spring that can be the same tension spring that shortens the LAA occluder axially and that causes it to expand radially when it is unconstrained. As discussed, the interior cavities formed by the braided bodies of one or both implants can be filled with fabric, graft or other material configured to facilitate sealing and isolation of the LAA from the volume of the adjacent atrium. The delivery catheter can then be unscrewed from the coupling at the proximal end of the proximal implant and be withdrawn over the guidewire. The guidewire can then be withdrawn.

Figure 13:
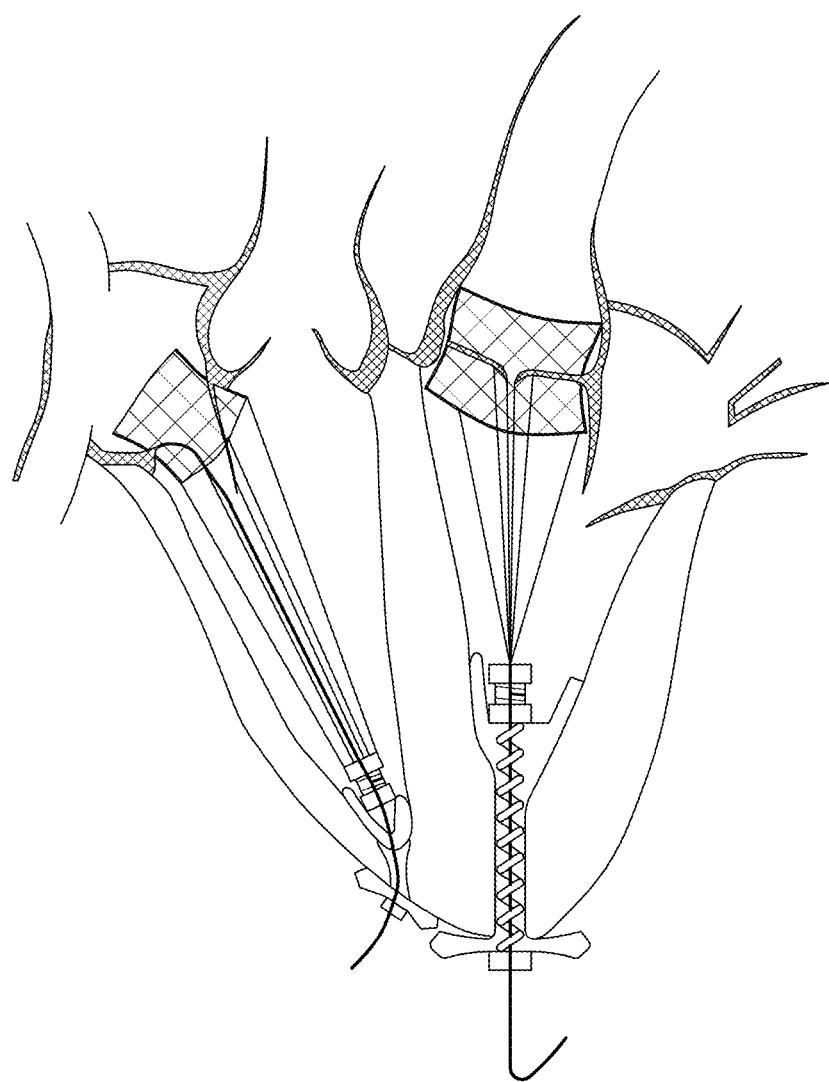
FIG. 13 is a schematic view of a further system in accordance with the present disclosure to deliver an implant to the left ventricle of a patient to anchor an artificial mitral valve.

FIG. 13 is a schematic view of a further system in accordance with the present disclosure to deliver an implant to the left ventricle of a patient to anchor an artificial mitral valve. As depicted, the delivery sequence is similar to that of the previous figures, wherein an anchor is first delivered into, and preferably through, the apex of the left ventricle. As depicted, first, an anchor, such that in FIG. 1D of Ser. No. 15/664,642, is disposed through the cardiac tissue in the apex of the left ventricle with the distal disc being located in the pericardial cavity outside the left ventricle, and the proximal disc being located inside the heart within the apex of the left ventricle, wherein the two discs are pulled toward each other by a tension spring, as depicted in FIG. 12 with the guidewire passing through the center of the tension spring. The proximal end of the implant includes a threaded male or female fastener that functions as a docking collar. Procedurally, the guidewire is first advanced through the apex of the left ventricle into the pericardial cavity, and the implant is installed in the wall. Once it has been confirmed that the implant is firmly seated, it can serve as an anchor, and a docking station, to install an artificial mitral valve that partially or fully replaces the native mitral valve. As with the embodiment of FIG. 12, the delivery catheter that delivers the anchor across the wall of the apex of the left ventricle can be unscrewed from the implant and withdrawn over the guidewire, and a second delivery catheter can be delivered over the guidewire with the artificial valve. The distal structure of the artificial valve can terminate in a complementary male or female threaded coupling that is then threadably received by the docking collar of the implant that has been installed in the apex of the left ventricle. The retractable sheath of the delivery system (not shown) can be withdrawn to first expose one or more chordae coupled to the threaded coupling, and then that permits the valve to deploy in the mitral annulus. Native mitral valve leaflets can be compressed out of the way by the expanding implant and/or cut out of the way prior to installation. The mitral implant can be expanded to occupy the mitral annulus. The valve can further be held in place by various anchoring arrangements as known in the art, or as set forth in U.S. Pat. No. 10,321,998, which is incorporated by reference herein in its entirety for all purposes. The structure of a valve prosthesis as set forth herein can also be made in accordance with the teachings of U.S. Pat. No. 10,321,998. Additionally, the structure of the valve prosthesis can also be made in accordance with the teachings of U.S. Pat. No. 10,449,046 and U.S. Patent Application Ser. No. 10,398,551, each of which is incorporated by reference herein in its entirety for all purposes. Likewise, the valve prosthesis may be delivered to its respective annulus using rail fixation techniques and using delivery systems as set forth in U.S. Pat. Nos. 10,321,998, 10,449,046 and U.S. Patent Application Ser. No. 10,398,551. The chordae may extend from the coupling attached to the anchoring implant in the apex of the left ventricle to one or more leaflets formed into the replacement valve, and/or to a peripheral structural frame of the replacement valve. If desired, prior to implanting the artificial mitral valve, a cerclage implant can be installed about the mitral valve as set forth in U.S. patent application Ser. No. 15/796,344 to form a landing zone or reinforced mitral annulus for the replacement valve to urge against.

FIG. 13 also discloses a similar delivery and implantation of a distal anchor across the wall of the heart in the apex of the right ventricle, similarly coupled to an artificial tricuspid valve by way of one or more chordae. As with the embodiment of the left ventricle, the anchor can be delivered first and implanted. Once the anchor is secured, the guidewire can be left in place, along with a pushrod disposed around the guidewire to permit the anchor to be collapsed and repositioned or removed (as with the embodiment of FIG. 12), as desired. The valve can be delivered over the guidewire and/or push rod and secured, such as by threaded connection or other means, to the anchor. The artificial tricuspid valve can then be deployed. The artificial tricuspid valve can be a partial prosthesis that replaces some of the leaflets, or it may replace the entire native tricuspid valve. If desired, either implant system illustrated for the mitral or tricuspid valve can also be integral, wherein the anchor is attached to the artificial valve prior to implantation.

As discussed, the interior cavities of the anchors of FIG. 13 can be formed by the braided bodies of the implant located in the apex of the left ventricle can be filled with fabric, graft or other material configured to facilitate sealing and isolation of the LAA from the volume of the adjacent atrium. The relative placement of the guidewire is illustrated prior to its being withdrawn at the end of the procedure. It will be appreciated that the distal implant can be deployed across a tissue structure to act as an anchor in a variety of applications and that a variety of different devices can be coupled to the distal anchor, such as occluders and artificial valves as illustrated herein, or filter structures, embolic protection devices, valve leaflets, cardiac pacing leads, and the like. For example, a distal anchor can be provided with a plurality of pacing electrodes (not specifically illustrated). Such an anchor can be coupled thereafter to a pacing lead that can transmit electrical signals to and from the anchor/pacing lead.

Figure 14A:
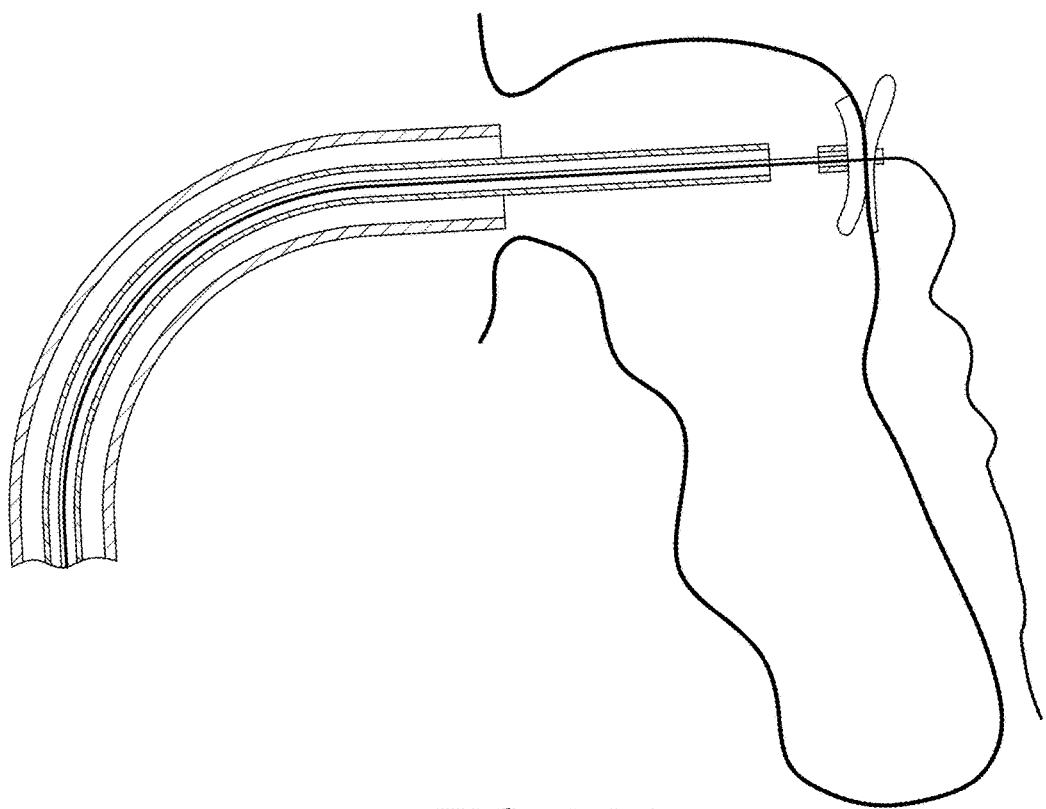
FIGS. 14A-14C are schematic views of illustrative method steps to implant a structure similar to the embodiments of FIG. 12 in accordance with the present disclosure.
Figure 14B:
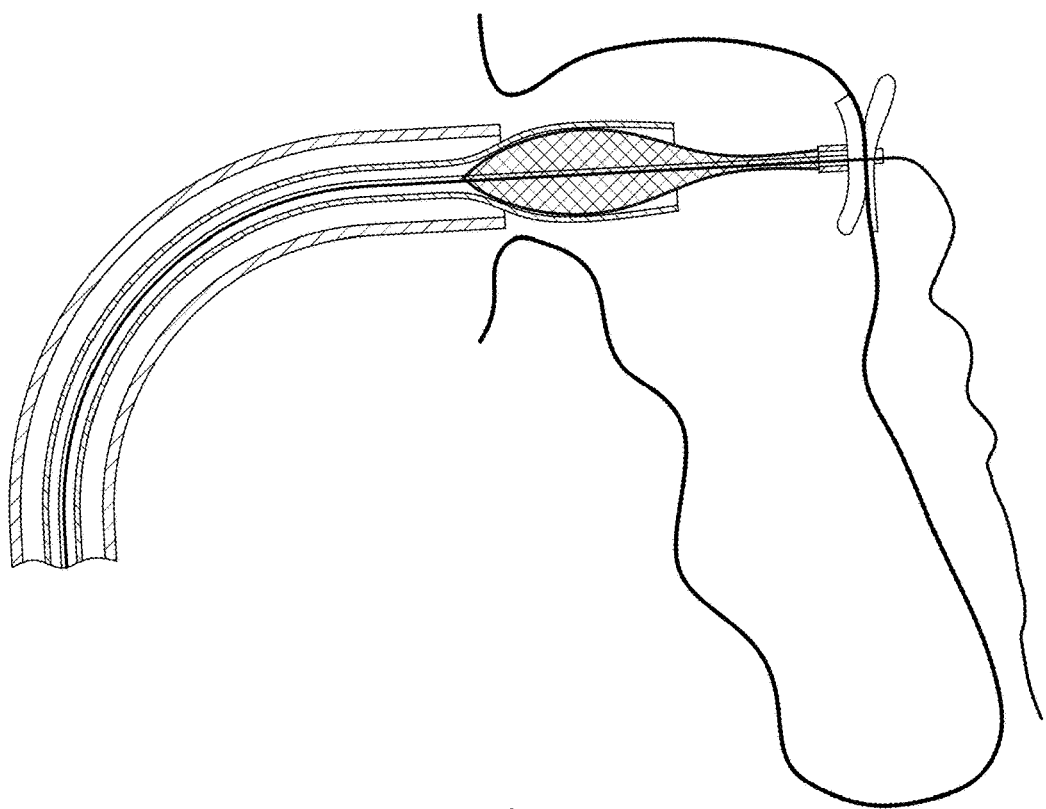
Figure 14C:
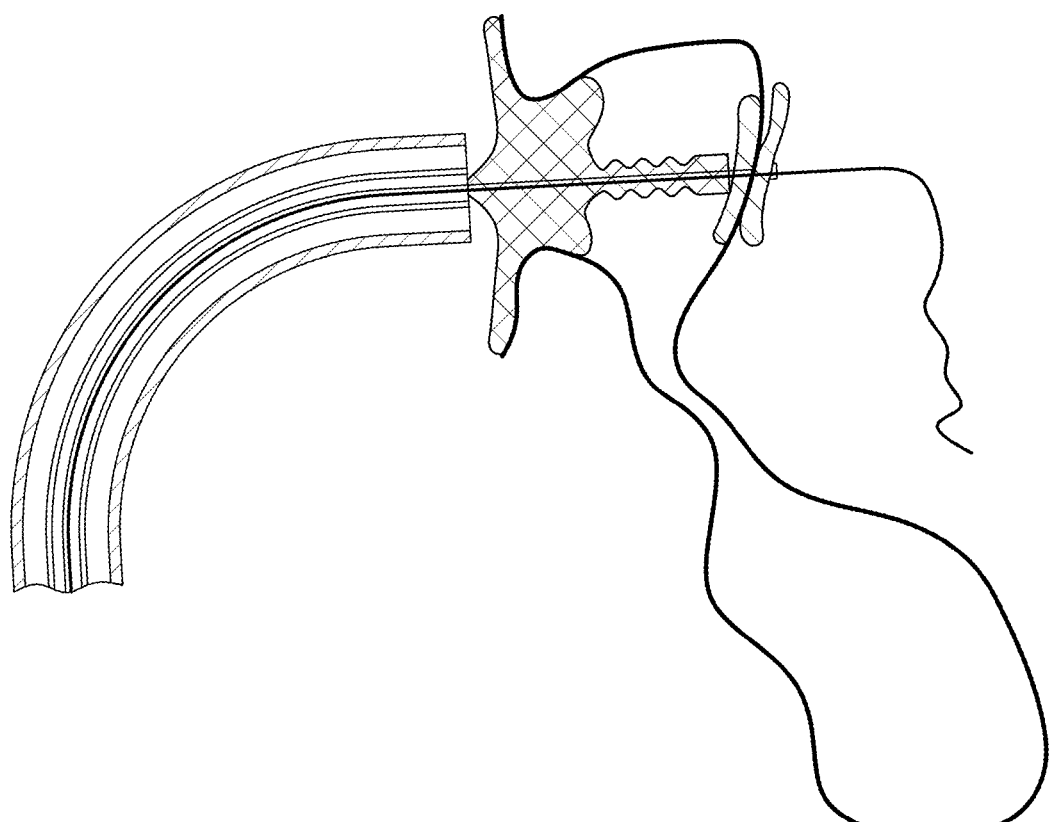

For purposes of illustration, and not limitation, FIGS. 14A-14C are schematic views of illustrative method steps to implant a structure similar to the embodiment of FIG. 12 in accordance with the present disclosure.

As depicted in FIG. 14A, a microcatheter including an external anchor, such as that depicted in FIG. 1D of U.S. Ser. No. 15/664,642 and a delivery system including a push tube 180 as set forth in FIG. 1C of U.S. Ser. No. 15/664,642 rod can be advanced over a guidewire that has previously been advanced through the wall of the LAA and into the pericardial space. Distal and proximal discs of the anchor implant are deployed sequentially by pulling the push tube and then the microcatheter back respectively to permit the discs to become unconstrained and to expand. The distal anchor can be retrieved into the microcatheter with the help of the push rod if necessary as set forth in U.S. Ser. No. 15/664,642. The microcatheter can then be withdrawn, leaving the guidewire in place. Alternatively, the microcatheter can be withdrawn over the push tube, wherein the push tube remains in place over the guidewire.

As depicted in FIG. 14B, a delivery system including the LAA occluder device can be advanced over the same guidewire, and over the push tube if the push tube is still in place. Leaving the push tube in place adds rigidity to the construction and makes it easier to align the threading of the proximal LAA occluder with the docking collar of the external anchor to facilitate alignment of the threading or other coupling of the LAA occluder to the threading or other coupling of the previously installed anchor.

As depicted in FIG. 14C, the LAA occluder is deployed by pulling back the delivery system. A tension spring or other suitable elastic member that preferably runs the length of the LAA occluder and runs through the distal tail of the LAA occluder pulls on the distal anchor and also causes the LAA to compress along an axial direction and expand radially outwardly to fill the transverse width of the left atrial appendage. Leaving the push tube in place over the guidewire and extending into the distal anchor secured to the LAA wall makes it possible to retrieve the whole system if it is needed. If the push tube were removed, it can still be reintroduced by sliding it over the guidewire. It will be appreciated that delivery of the anchor and artificial valve of FIG. 13 can be accomplished in a similar manner.

In some implementations, the prosthesis can be made in whole or in part from bioresorbable materials. Suitable bioresorbable materials and techniques for construction can be found, for example, in U.S. patent application Ser. No. 11/398,363, filed Apr. 4, 2006, and U.S. patent application Ser. No. 14/461,159, filed Aug. 5, 2014, each of which is incorporated by reference herein in its entirety for all purposes.

The devices and methods disclosed herein can be used for other procedures for closing openings in tissue, such as hollow organs and the like, in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure.

The invention claimed is:

1. An implant to occlude a left atrial appendage (LAA) in a heart, comprising:
    a distal anchor having a first expanded portion configured to be situated in a pericardial cavity of a heart and a second expanded portion configured to be situated inside a LAA, wherein a neck portion of the distal anchor is configured to traverse an opening formed in a wall of the LAA from inside the heart into the pericardial cavity; and
    a LAA occluder configured to be expanded into the LAA to occlude a substantial volume of the LAA, the LAA occluder being removably coupled to the distal anchor, wherein a relative distance between the first expanded portion of the distal anchor and the LAA occluder can be adjusted.

2. The implant of claim 1, wherein the LAA occluder is configured to be removably coupled to the distal anchor by a threaded connection.

3. The implant of claim 1, wherein the LAA occluder is configured to be removably coupled to the distal anchor by a keyed connection.

4. The implant of claim 1, wherein the LAA occluder is configured to be removably coupled to the distal anchor by a lock.

5. The implant of claim 1, wherein the LAA occluder is coupled to at least one length limiting tether that connects to a fastener that is configured to couple to the distal anchor.

6. The implant of claim 1, wherein the first expanded portion of the distal anchor is configured to be displaceable proximally or distally with respect to the LAA occluder during implantation.

7. The implant of claim 1, wherein the distal anchor is formed from at least one expandable braided disc.

8. The implant of claim 1, wherein the distal anchor and LAA occluder are connected at least in part by a tension spring that pulls the distal anchor toward the LAA occluder.

9. The implant of claim 1, wherein the distal anchor and LAA occluder are connected at least in part by at least one length limiting tether.

10. The implant of claim 1, further comprising at least one tether directed through the LAA occluder configured to be coupled to the distal anchor, wherein applying tension to the at least one tether draws the LAA occluder and first expanded portion of the distal anchor closer together.

11. A system including a delivery catheter having a proximal end and a distal end, a distal end of the delivery catheter being coupled to the implant of claim 1, wherein the distal anchor of the implant is configured to be pulled with respect to the LAA occluder by the delivery system to create tension between the LAA occluder and the distal anchor.

12. The system of claim 11, further comprising a lock to lock the distal anchor to the LAA occluder to maintain the relative position of the distal anchor to the LAA occluder.

13. The system of claim 11, wherein the LAA occluder and the distal anchor are connected by way of a hollow tether.

14. A method of treating a left atrial appendage, comprising:
    anchoring a distal anchor of the implant using the system according to claim 11 across the wall of the left atrial appendage of a patient;
    disposing the distal end of the delivery catheter proximate a left atrial appendage (LAA) of a patient;
    coupling the LAA occluder to the distal anchor; and
    deploying the LAA occluder to isolate an interior volume of the LAA from the left atrium.

15. The method of claim 14, further comprising locking the LAA occluder and the distal anchor in a relative position with respect to each other.

16. The method of claim 15, further comprising unlocking the LAA occluder from the distal anchor and adjusting the relative position of the LAA occluder to the distal anchor.

* * * * *